(12) United States Patent
Rousseau

(10) Patent No.: US 6,551,356 B2
(45) Date of Patent: Apr. 22, 2003

(54) POCKETED HERNIA REPAIR

(75) Inventor: Robert A. Rousseau, Ottsville, PA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/812,194

(22) Filed: Mar. 19, 2001

(65) Prior Publication Data

US 2002/0133236 A1 Sep. 19, 2002

(51) Int. Cl.$^7$ .................................................. A61F 2/02
(52) U.S. Cl. ............................. 623/23.72; 623/11.11; 606/151
(58) Field of Search ....................... 606/151; 623/23.72, 623/11.11; 128/112.1, 899, 106.1, 107.1

(56) References Cited

U.S. PATENT DOCUMENTS

| | | |
|---|---|---|
| 2,671,444 A | 3/1954 | Pease, Jr. |
| 3,054,406 A | 9/1962 | Usher |
| 4,141,515 A | 2/1979 | Lock et al. |
| 4,347,847 A | 9/1982 | Usher |
| 4,452,245 A | 6/1984 | Usher |
| 4,561,434 A | 12/1985 | Taylor |
| 4,854,316 A | 8/1989 | Davis |
| 5,059,205 A | 10/1991 | El-Nounou et al. |
| 5,116,357 A | 5/1992 | Eberbach |
| 5,122,155 A | 6/1992 | Eberbach |
| 5,147,374 A | 9/1992 | Fernandez |
| 5,147,384 A | 9/1992 | La Rocca |
| 5,254,133 A | 10/1993 | Seid |
| 5,258,000 A | 11/1993 | Gianturco |
| 5,290,217 A | 3/1994 | Campos |
| 5,356,432 A | 10/1994 | Rutkow et al. |
| 5,368,602 A | 11/1994 | de la Torre |
| 5,370,650 A | 12/1994 | Tovey et al. |
| 5,397,331 A | 3/1995 | Himpens et al. |
| 5,425,740 A | 6/1995 | Hutchinson, Jr. |
| 5,456,720 A * | 10/1995 | Schultz et al. ................ 623/12 |
| 5,634,931 A | 6/1997 | Kugel |
| 5,697,978 A * | 12/1997 | Sgro ............................ 623/12 |
| 5,716,409 A * | 2/1998 | Debbas ........................ 623/11 |
| 5,741,297 A | 4/1998 | Simon |
| 5,743,917 A * | 4/1998 | Saxon ......................... 623/11 |
| 5,769,864 A | 6/1998 | Kugel |
| 5,813,975 A * | 9/1998 | Valenti ........................ 600/37 |
| 5,824,082 A | 10/1998 | Brown |
| 5,916,225 A | 6/1999 | Kugel |
| 5,922,026 A | 7/1999 | Chin |
| 6,042,534 A * | 3/2000 | Gellman et al. .............. 600/30 |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,241,768 B1 * | 6/2001 | Agarwal et al. ......... 623/11.11 |
| 6,270,530 B1 * | 8/2001 | Eldridge et al. ......... 623/23.74 |
| 6,287,316 B1 * | 9/2001 | Agarwal et al. ............ 606/151 |
| 6,290,708 B1 * | 9/2001 | Kugel et al. ................ 606/151 |

OTHER PUBLICATIONS

US 5,318,559, 6/1994, Mulhauser et al. (withdrawn)

* cited by examiner

Primary Examiner—Bruce Snow
Assistant Examiner—Cheryl L Miller

(57) ABSTRACT

A device for surgically repairing and reinforcing a hernia includes a hernia prosthesis having a substantially planar base portion and an overlay portion, each formed from a biocompatible material. The overlay portion is peripherally attached to the base portion to define a pocket to receive a surgical instrument or a surgeon's finger for placing the prosthesis within the human body. The pocket may be formed with releasable stitching to enable it to be flattened or removed after placement and may contain a resilient member that urges the prosthesis into a flat configuration.

5 Claims, 4 Drawing Sheets

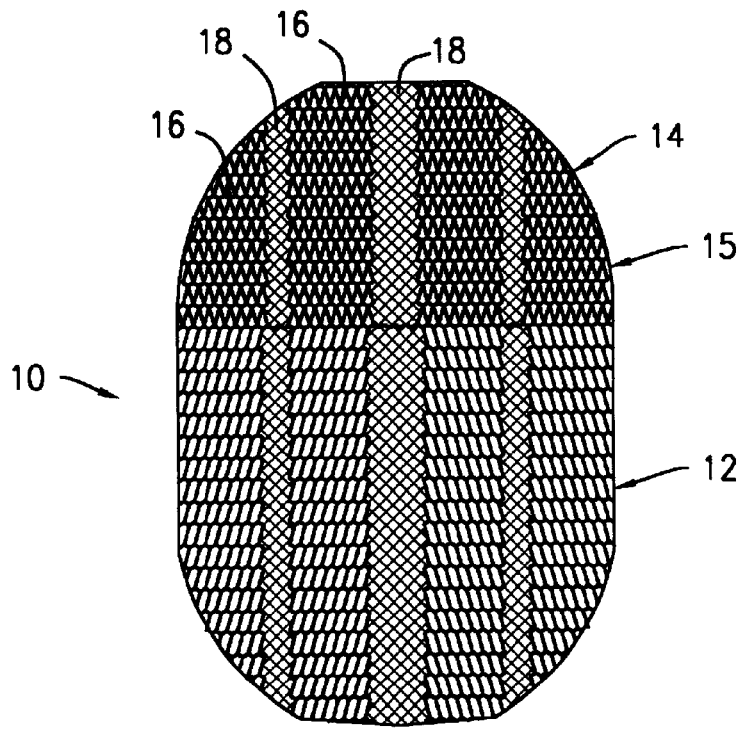
FIG. 1
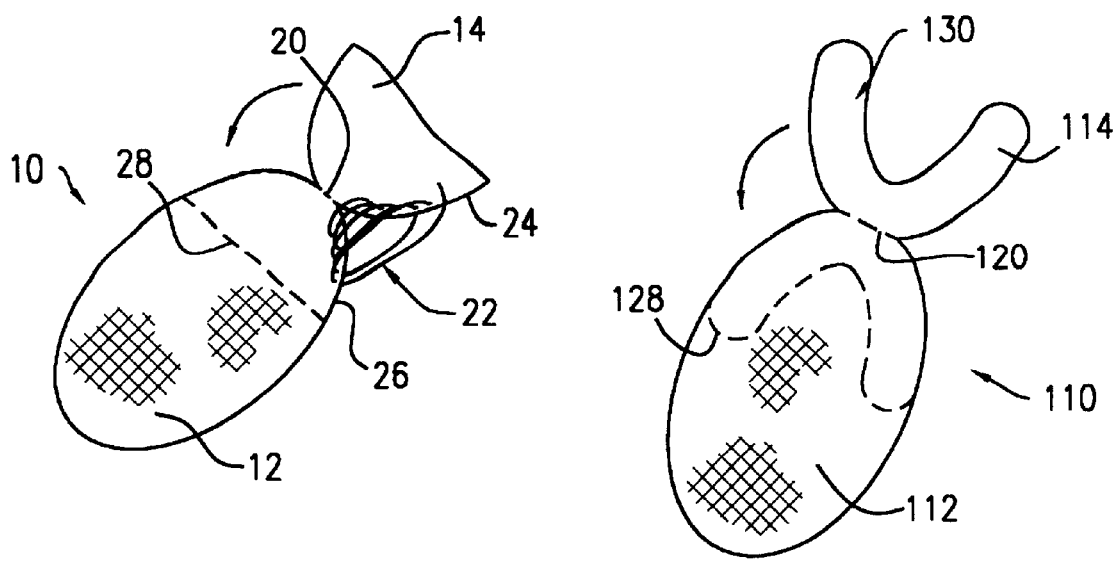
FIG. 2
FIG. 3

POCKETED HERNIA REPAIR

FIELD OF THE INVENTION

The present invention relates to a hernia repair prosthesis, and more particularly to a substantially planar surgical mesh prosthesis for bridging a hernia.

BACKGROUND OF THE INVENTION

Surgically implantable mesh patches for the repair of inguinal and other abdominal wall hernias are commonly used and provide tension free repairs by bridging the hernia defect. Patches of this type constitute a structural support which decreases recurrence rates and because they do not require the displacement of tissues to cover the hernia, decrease postoperative discomfort. Frequently, prostheses of this type are sutured in place, i.e., proximate to the periphery of the patch. An alternative to suturing the prosthesis is to insert it into the properitoneal space. U.S. Pat. No. 5,916,225 to Kugel discloses a hernia prosthesis having a resilient ring made of synthetic material, such as nylon, polypropylene or polyester enclosed within a pocket formed by opposing planar segments of surgical mesh that are attached together to encapsulate the ring. A slit is provided in one of the planar segments to permit the surgeon to insert a finger therein in order to push the prosthesis through an incision in the abdominal wall into the properitoneal space and across the hernia. The resilient ring urges the pocket into a deployed planar configuration, i.e., to straighten the wrinkling and folding of the pocket that occurs in the course of its placement. The disadvantages associated with the device disclosed in U.S. Pat. No. 5,916,225 are that each layer of mesh is stiff and dense, such that the combination of two layers and the resilient ring constitutes a rigid, high mass prosthesis which tends to cause discomfort and resists conformance to the patient's anatomy.

It is therefore an object of the present invention to provide a hernia repair prosthesis for use in a surgical hernia repair as generally described in U.S. Pat. No. 5,916,225 but that has lower mass, and greater flexibility.

SUMMARY OF THE INVENTION

The problems and disadvantages associated with conventional hernia prostheses and their associated methods of use are overcome by the present invention which includes a hernia prosthesis having a substantially planar base portion and overlay portion, each formed from a biocompatible material. The overlay portion is attached to the base portion in substantially parallel juxtaposition thereto and along an attachment junction that defines an open ended pocket therebetween. The open-ended pocket receives an elongated object such as a surgical instrument or a surgeon's finger for placing the prosthesis within the human body. The pocket captures an end of the elongated object when it is urged in a first direction to induce the displacement of the prosthesis in the first direction and slidably releases the elongated object when it is moved in the opposite direction.

BRIEF DESCRIPTION OF THE FIGURES

For a better understanding of the present invention, reference is made to the following detailed description of several exemplary embodiments considered in conjunction with the accompanying drawings, in which:

FIG. 1 is a plan view of a hernia prosthesis in accordance with a first exemplary embodiment of the present invention.

FIG. 2 is a diagrammatic, perspective view of the prosthesis of FIG. 1 in a partially assembled state;

FIG. 3 is a diagrammatic, perspective view of a prosthesis in accordance with a second exemplary embodiment of the present invention;

DESCRIPTION OF THE PREFERRED EMBODIMENTS

Figure 4:
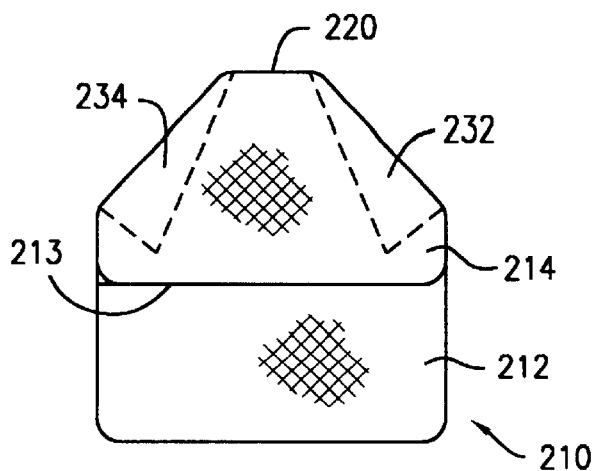
FIG. 4 is a is plan view of a hernia prosthesis in accordance with a third exemplary embodiment of the present invention.

FIGS. 1 and 2 show a prosthesis 10 in accordance with the present invention having a generally planar base portion 12 and an overlay portion 14, folded thereover to form a pocket 15. The pocket 15 is dimensioned to receive the finger of a surgeon, as shall be explained below. The prosthesis 10 may be formed from any biologically compatible, flexible, porous medical textile, such as those commonly used for reinforcing and occluding tissue defects. Knitted polypropylene monofilament mesh fabrics such as those available from Ethicon, Inc. under the PROLENE, VICRYL and PANACRYL trademarks may be utilized to fabricate the prosthesis 10. Other suitable mesh materials are available under the MARLEX, DACRON, TEFLON, MERSELENE, and POLYSORB (produced by United State Surgical Corporation) trademarks. Tissue regeneration may be induced through the use of absorbable materials in fabricating the prosthesis 10. It is preferred that the mesh used to form the prosthesis 10 be simultaneously flexible and have a low mass with a high porosity/open area ratio. These objectives are met by a material described in a copending application entitled KNITTED SURGICAL MESH, application Ser. No. 09/723,854 filed Nov. 28, 2000 and owned by the assignee of the present application, such application being incorporated herein by reference. The foregoing material is commercially available from Ethicon, Inc. under the trademark PROLENE*SOFT.

The prosthesis 10 preferably has visible alternating stripes 16, 18 or other indicia to aid in identifying the orientation of the prosthesis 10 when it is being placed in the body of the patient. While a circular prosthesis 10 may be used in certain circumstances, in other situations an oblong or oval shape, having a greater extent in one dimension is preferred. Accordingly, the stripes 16, 18 may be used to orient an elongated prosthesis 10 at the surgical site, e.g., by presenting a readily appreciable indicia of orientation. The stripes 16, 18 may be provided by utilizing a pattern of different color fibers in the textile from which the prosthesis 10 is made. Alternatively, stripes or other indicia may be printed on or otherwise applied to the prosthesis 10.

The overlay portion 14 has a complementary shape to that of the base 12, such that when the overlay portion 14 is folded along fold line 20, the respective outer peripheral edges 24, 26 align and may be bonded by adhesives, plastic welding, interweaving or by being stitched together by thread 22. The stitching of the thread 22 may be interlocking to prevent the removal of the thread 22 or the thread may be removable by pulling on a free end thereof to unravel removable stitching, as further described below. The use of removable stitching permits the thread 22 to be removed after placement of the prosthesis at the hernia repair site and the subsequent unfolding and flattening of the overlay portion 14 to a position substantially co-planar with the base 12. In this manner, the thickness and rigidity of the prosthesis 10 can be reduced and the extent thereof can be increased by the unfolding, i.e., by the length of the overlay portion 14. The extent of overlap of the overlay portion 14, relative to the base 12, when in the folded configuration, is illustrated in FIG. 2 by dotted line 28.

FIG. 3 shows a prosthesis 110 in accordance with an alternative embodiment of the present invention, in which the overlay portion 114 has a generally U-shaped configuration, with a central scallop 130. Elements illustrated in the alternative embodiments shown in FIGS. 3–10 which correspond to elements described above with respect to FIGS. 1 and 2 have been designated by corresponding reference numerals increased by 100, 200, 300 and 400, respectively. The position of the overlay portion 114 on the base 112 when folded along fold line 120 is illustrated by dotted profile line 128. The scallop 130 reduces the mass and rigidity of the overlay portion 114 while preserving a structure that will capture an inserted finger when urged in the forward and sideways directions to allow positioning of the prosthesis 110. In addition, the scallop increases the degree of freedom of the inserted finger. For example, while a straight-edged overlay portion 14 like that shown in FIG. 1 (see line 28) may restrain the inserted finger from bending at the first and/or second joint, the U-shaped overlay portion 130 would permit bending of the finger at these joints.

Figure 5:
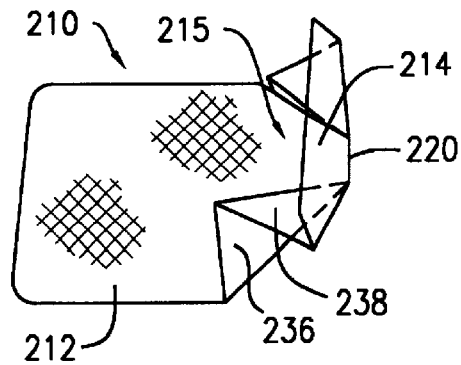
FIG. 5 is a is perspective view of the prosthesis of FIG. 4, at an intermediate stage of folding.

FIGS. 4 and 5 illustrate an alternative prosthesis 210 that is formed from a substantially rectangular piece of surgical mesh. As before, the overlay portion 214 is folded at line 220 over the base 212. In order to form a generally pointed configuration where the prosthesis is narrower at the fold 220 than at the free end 213 of the overlay 214, folds 232, 234 each having at least two panels 236, 238, extend inwardly between overlay portion 214 and the base 212. The pointed shape of the folded prosthesis 210 aids in introducing it through the patient's tissues to the hernia site. As in the previous embodiments, the overlay portion 214 may be either fixedly or removably bonded to the base 212. Because the shape of the prosthesis 210 is realized by folding, if the bonding is removable, the prosthesis 210 may be unfolded to a generally rectangular planar shape, thereby minimizing rigidity and maximizing surface area.

Figure 6:
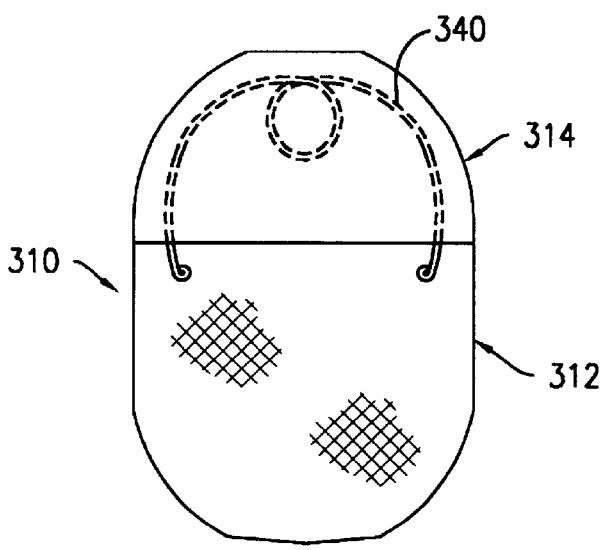
FIG. 6 is a plan view of a hernia prosthesis in accordance with a fourth exemplary embodiment of the present invention.
Figure 7:
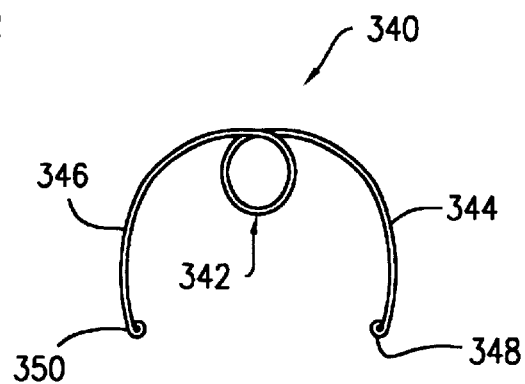
FIG. 7 is a plan view of a elastic stretcher element used in the prosthesis of FIG. 6.

FIGS. 6 and 7 show an alternative embodiment of the present invention having a prosthesis 310 such as that disclosed above in reference to FIGS. 1–5 but with a resilient spreader element 340 inserted between overlay portion 314 and base portion 312. The resilient member 340 may be a simple U-shaped spring made from stainless steel, super elastic steel, such as, NiTi NOL, or plastic, such as, nylon. The resilient member 340 is deformable to allow the prosthesis 310 to be placed proximate to the hernia. Once in position, the resilient member 340 urges the prosthesis 310 into a generally planar configuration extending over the hernia defect. The resilient member 340 shown in FIGS. 6 and 7 has a central loop 342 to increase its flexibility and to provide a means for grasping the resilient member 340, i.e., the loop 342 can receive the finger of a surgeon inserted therein. The resilient member 340 may also be provided with end loops 348, 350 through which the resilient member 340 may be attached to the prosthesis 310 by stitching, i.e., in those circumstances when the surgeon would prefer the resilient member 340 to remain in the prosthesis 310 at the end of the procedure. Alternatively, the resilient member 340 may be removable, either being tucked between the overlay portion 314 and the base portion 312 or held to the prosthesis 310 by removable stitching. When the prosthesis 310 has been placed and the resilient member 340 has accomplished its purpose of spreading the prosthesis over the hernia site, then the resilient member 340 may be removed to decrease the mass and rigidity of the prosthesis 310 and any associated discomfort. During removal, the end loops 348, 350 prevent the ends of the arms 344, 346 of the resilient member 340 from piercing or snagging on the adjacent tissues. As shown in FIG. 6, the end loops 348, 350 may extend beyond the overlay 314. In this manner, the resilient member 340 exerts its flattening effect over a larger surface area of the prosthesis 310, i.e., beyond overlay flap 314.

Figure 8:
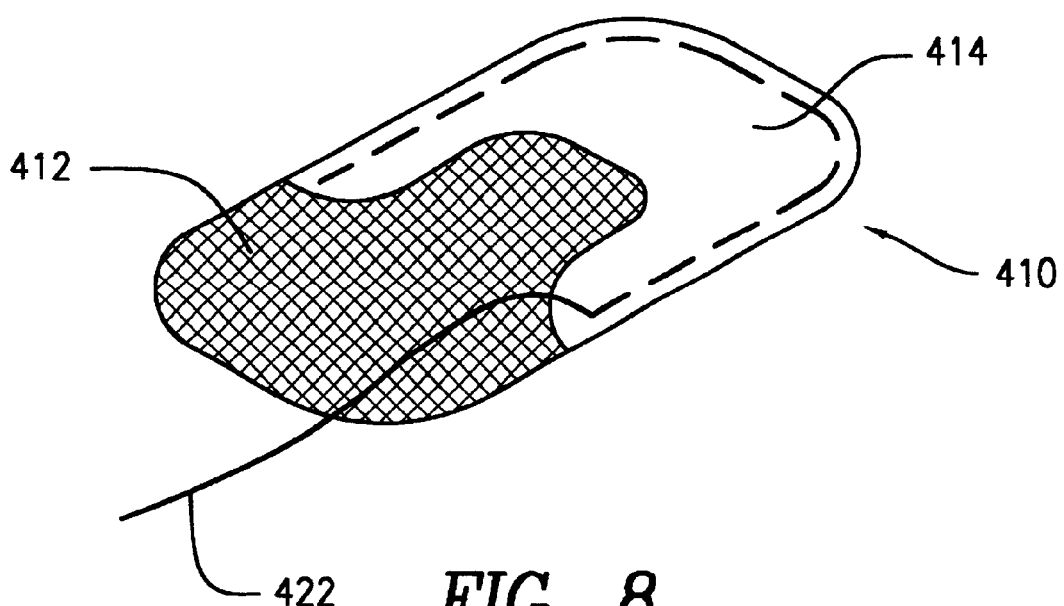
FIG. 8 is a perspective view of a prostheses in accordance with a fifth exemplary embodiment of the present invention.
Figure 9:
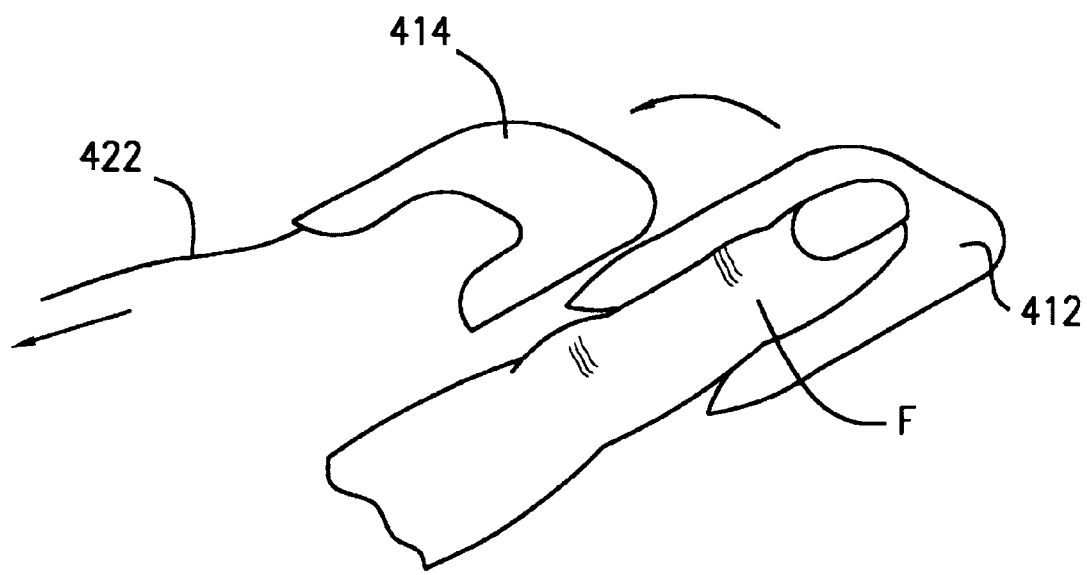
FIG. 9 is a diagrammatic view of the disassembling of the prosthesis of FIG. 8.
Figure 10:
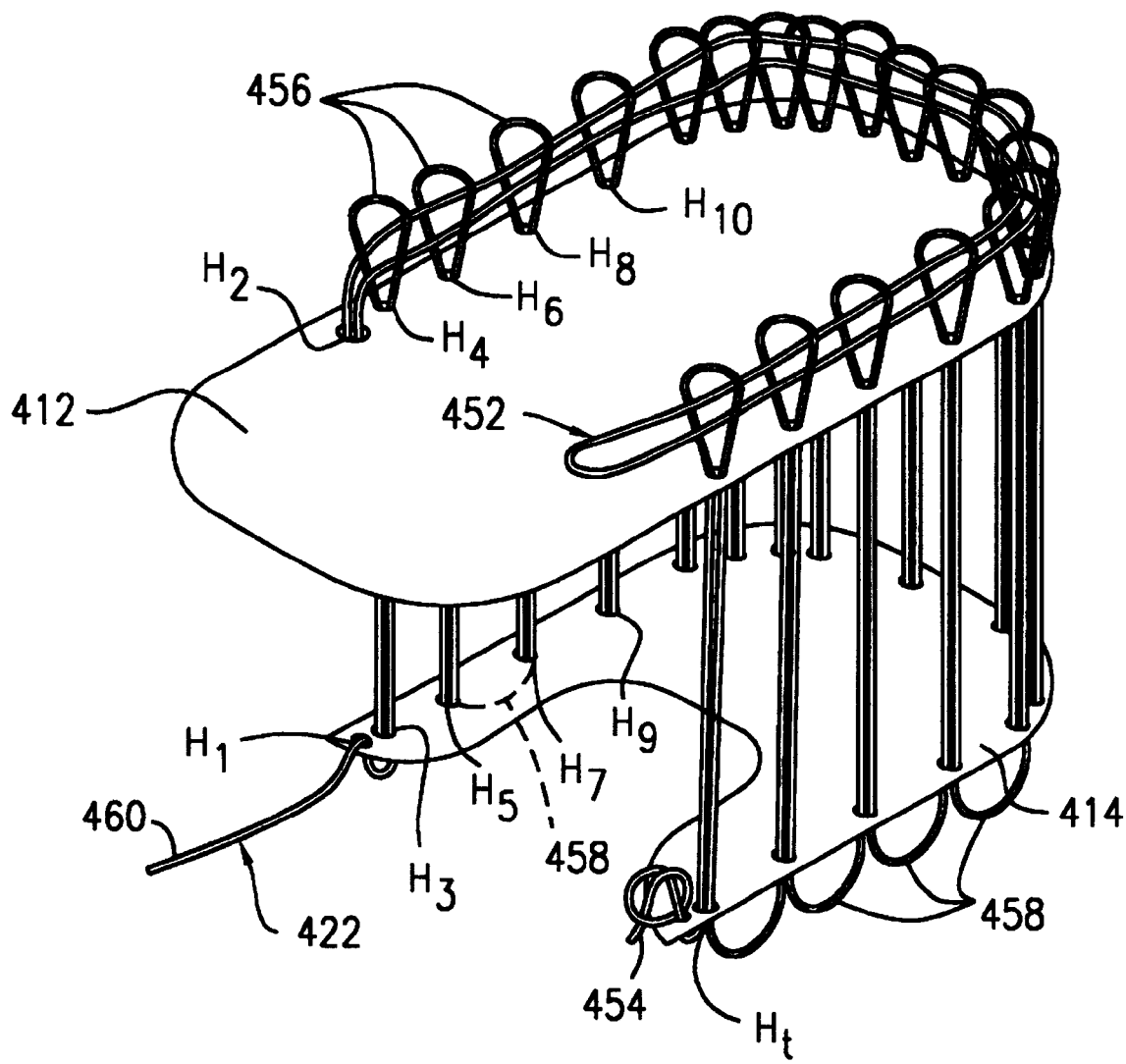
FIG. 10 is a perspective view of the prosthesis of FIG. 8 with the stitching unloosened to illustrate a releasable stitching arrangement.

FIGS. 8–10 show a prosthesis 410 in accordance with the present invention and having an overall configuration similar to that of the forgoing embodiments depicted in FIGS. 1–7, but having a separate overlay portion 414 that is entirely detachable from the base portion 412. More particularly, the overlay 414 is a separate piece of surgical mesh that is held to the base 412 by thread 422 that stitches the overlay 414 to the base 412 in a releasable manner. FIG. 9 illustrates that when the thread 422 is pulled to release the stitching holding the overlay 414 to the base 412, the thread 422, upon further pulling, may be used to remove the overlay from its position relative to the base 412. During the placement of the prosthesis 410, the surgeon's finger F may be held over the base 412 to retain it in a selected position whereupon the thread 422 may be pulled releasing and removing the overlay portion 414 from the base portion 412. In this manner, the overlay portion 414 may be utilized in the process of placing the prosthesis 410 into position, i.e., by forming a gripping pocket and then detached to decrease the rigidity and mass of the prosthesis 410 to a single layer of mesh. i.e., the base portion 412.

FIG. 10 shows one exemplary method of implementing a removable stitching arrangement to releasably retain the overlay 414 in association with the base 412. More particularly, the thread 422 is passed through a first hole $H_1$ in the overlay portion 414 and then through a corresponding hole $H_2$ in the base portion 412. (While the overlay 414 and base 412 are shown spaced apart in FIG. 10, this is for the purpose of illustration only. In forming the prosthesis 410, they would be juxtaposed.) An elongated release loop 452 is formed and the distal end 454 of the release loop 452 is then passed through hole $H_3$ and $H_4$. The distal end 454 is then looped over the release loop 452 to form a gripper loop 456 and then reenters hole $H_4$ and then hole $H_5$. The distal end 454 is then passed to hole $H_7$ to form an overlay retainer loop 458 (shown in dotted lines proximate hole $H_7$). This pattern is repeated multiple times until the terminal end 454 reaches the terminal hole Ht where it is tied off against the overlay portion 414. When the proximal end 460 of the thread 422 is pulled, the release loop 452 is pulled through the gripper loops 456, allowing them to be pulled through the even numbered holes $H_4$, $H_6$, etc. This allows the retainer loops 458 to be pulled from the odd numbered holes $H_5$, $H_7$, etc. After all the gripper and retainer loops 456, 458 are pulled out, the overlay 414 is pulled free of the base 412 by the thread 422, as shown in FIG. 9.

The prosthesis 10 may be used in the surgical repair of a hernia in accordance with the procedure described in U.S. Pat. No. 5,916,225 to Kugel, such patent being incorporated herein for its teaching relative to this procedure, which is also known in the art. Briefly, the repair of an inguinal hernia is made in accordance with this known procedure utilizing the present invention by inserting the prosthesis 10, 110, 210, 310 or 410 through a relatively small, oblique incision, e.g., 2 to 3 centimeters in length, made in the patient's abdomen above the internal ring location of the inguinal hernia. To prepare for insertion of the prosthesis, the surgeon performs a dissection through the oblique incision deep into the patient's pro-peritoneal space, using the muscle splitting technique. This dissection process results in a pocket in the pro-peritoneal space that can receive the prosthesis 10. The prosthesis 10 (or 110, 210, 310 or 410) of the present invention can be placed over the surgeon's finger or fingers, i.e., with the finger(s) in the pocket 15. The prosthesis 10 is then inserted into the cavity previously surgically formed in the pro-peritoneal space. If the prosthesis is inadvertently folded in the course of placement in the body, it can be unfolded by the surgeon's finger(s) or under the influence of the resilient member 340. This unfolding operation is aided by the overlay portion 14 which provides a means for the surgeon to push the distal edge at fold line 20 forward, as well as to push against the sides (proximate to the peripheral edges 24, 26) of the prosthesis 10. This allows the surgeon to position the prosthesis 10 to the best advantage for supporting the herniated tissue. In the event that a resilient member 340 is utilized, it may be removed after placement of the prosthesis 310. Furthermore, if removable stitching is employed, (formed by thread 422), the overlay portion 414 may be unfolded (as in the embodiments of FIGS. 1–5) or removed (as in the embodiment of FIGS. 8–10). While the foregoing procedure of placing the prosthesis 10 utilizes the surgeon's finger(s) directly, one or more surgical instruments could be employed to position and flatten the prosthesis. For example, one or a pair of steel rods can be used in the same manner as the surgeon's finger(s). The pair of rods may be independent or conjoined at a pivot point, such that the spacing of the distal ends thereof may be controlled by the spacing of the proximal ends.

It should be understood that the embodiments described herein are merely exemplary and that a person skilled in the art may make many variations and modifications without departing from the spirit and scope of the invention as defined in the appended claims. Accordingly, all such variations and modifications are intended to be included within the scope of the invention as defined in the appended claims. For example, while the embodiments described above utilize an overlay portion 14 that is smaller in surface area than the base portion 12 and therefore only partially covers the base portion 12, the present invention could be carried out by a prosthesis that utilizes base and overlay portions that are of equal or substantially equal dimensions.

I claim:

1. A hernia prosthesis comprising:
   a substantially planar base portion formed from a biocompatible material;
   a substantially planar overlay portion formed from a biocompatible material and removably attached to said base portion in substantially parallel juxtaposition thereto by removable stitching having an elongated thread that threads through said base portion and said overlay portion at a plurality of points along an attachment junction that defines an open-ended pocket between said base portion and said overlay portion, said open-ended pocket being sized and shaped so as to receive an elongated object therein for placing said prosthesis within a human body, said open-ended pocket capturing an end of the elongated object when urged in a first direction to induce displacement of said prosthesis in the first direction and slidably releasing the elongated object when the elongated object is moved in a second direction, generally opposite to the first direction, said stitching drawing said base portion and said overlay portion together along said attachment junction preventing the elongated object from passing between said base portion and said overlay portion along said attachment junction, said overlay portion being selectively detachable from said base portion by removing said removable stitching, said elongated thread including a release loop of thread that permits said removable stitching to be removed, said release loop having a proximal end, a distal end and an intermediate loop portion, said intermediate loop portion being positioned adjacent an outer surface of one of said overlay and said base, said distal end passing through said outer surface at a plurality of locations forming a gripper loop at each of said plurality of locations, each of said gripper loops looping around said release loop, said release loop preventing said gripper loops from pulling through said outer surface, said distal end passing through a plurality of locations in the other of said overlay and said base forming retainer loops, said retainer loops in conjunction with said gripper loops holding said overlay in removable association to said base.

2. The prosthesis of claim 1, wherein said overlay portion only partially covers said base portion.

3. The prosthesis of claim 1, wherein said prosthesis is made from a knitted polypropylene monofilament mesh material.

4. The prosthesis of claim 1, wherein said distal end of said release loop is attached to said overlay to aid in the removal of said overlay when said stitching is removed to disassociate said overlay from said base.

5. The prosthesis of claim 1 wherein said distal end of said stitching is attached to said overlay to aid in the removal of said overlay when said stitching is removed to disassociate said overlay from said base.

* * * * *